United States Patent [19]

Masson

[11] 4,068,117

[45] Jan. 10, 1978

[54] LIGHTING PROJECTOR

[75] Inventor: André A. Masson, Saint-Heand, France

[73] Assignee: Etablissements Pierre Angenieux, Paris, France

[21] Appl. No.: 759,401

[22] Filed: Jan. 14, 1977

[30] Foreign Application Priority Data

| | | |
|---|---|---|
| Jan. 21, 1976 | France | 76.01538 |
| June 22, 1976 | France | 76.18912 |

[51] Int. Cl.$^2$ .......... A61B 1/06

[52] U.S. Cl. .......... 362/33

[58] Field of Search .......... 240/1.4, 41.15

[56] References Cited

U.S. PATENT DOCUMENTS

| | | | |
|---|---|---|---|
| 1,987,019 | 1/1935 | Logan | 240/1.4 |
| 3,225,184 | 12/1965 | Reiber | 240/1.4 |
| 3,437,803 | 4/1969 | Seitz et al. | 240/1.4 |

*Primary Examiner*—Leland A. Sebastian
*Attorney, Agent, or Firm*—Michael J. Striker

[57] ABSTRACT

This lighting projector, notably for surgical theaters, comprises a plurality of elongated basic elements extending radially from a central casing outwards and disposed by pairs in relative alignment and a light source for each pair of elements, disposed adjacent one of the two elements involved, with a pair of frosted zones adjacent said source, and a reflection mirror and an optical system adapted to form an image of said source on the field to be illuminated after reflecting said image on said mirror.

1 Claim, 4 Drawing Figures

LIGHTING PROJECTOR

BACKGROUND OF THE INVENTION

FIELD OF THE INVENTION

The present invention relates to a lighting projector of the type disclosed in the U.S. Pat. No. 3,848,119 and intended more particularly for surgical theatres and rooms.

Considering this specific purpose, this lighting projector is intended for eliminating cast shadows and providing a uniform illuminated field of high luminous intensite with a cold light and a minimum cross-sectional obstruction area.

For this purpose, this projector consists of a plurality of basic elements extending radially outwards from a central point, each element comprising in the direction from the centre to the outer end a light source, a frosted zone disposed in close vicinity of said source, and an optical member adapted to form the image of said light source in the plane to be illuminated after reflecting said image on an inclined reflection mirror.

Thus, the plane or field contemplated is illuminated by luminous beams reflected by the mirrors of the various basic elements of the projector, said mirrors being suitably oriented so that the axes of said beams converge towards a common point or spot corresponding to the centre of the field to be illuminated. All the light sources are grouped near the centre of the projector, thus facilitating the dissipation of the heat produced thereby.

DESCRIPTION OF THE INVENTION

It is the essential object of the present invention to reduce the number of the light sources in a projector of this character, while preserving a same number of basic elements. In fact, the cast shadows are eliminated by utilizing a plurality of basic elements delivering from their tips as many beams converging towards the field to be illuminated.

For this purpose, the basic elements of the lighting projector according to the present invention are distributed by pairs and disposed in diametrally opposite and aligned relationship in each pair, and furthermore there is provided a light source common to the elements of each pair and disposed adjacent one of the two elements concerned, two frosted zones being disposed on either side of said common light source and in close vicinity thereof.

Thus, the number of light sources and consequently the heat produced by the present projector are reduced appreciably without however decreasing the number of light beams directed towards the field to be illuminated.

A typical embodiment of this lighting projector will now be described with reference to the attached drawing, in which:

DESCRIPTION OF THE PREFERRED EMBODIMENT

As in the case of the lighting projector disclosed in the aforesaid U.S. Pat. No. 3,848,119, this lighting projector comprises a plurality of basic elements disposed radially about a central casing 5, but in the present case the basic elements 1, 2, 3 and 4 of this lighting projector are four in number and distributed by pairs, the two elements of a same pair being disposed in mutual axial alignment on either side of said central casing 5.

Each basic element comprises a tubular casing enclosing the optical components of the element and is rigid with the central casing 5. However, instead of comprising an individual light source for each base element (as in the case of the projector disclosed in the above-mentioned U.S. Pat. No. 3,848,119), the projector according to the instant invention comprises a light source common to each pair of basic elements disposed in relative axial alignment respectively. More particularly, in this embodiment two light sources *6a* and *6b* are provided instead of four in the aforesaid patent. In this invention, the first light source *6a* is common to both elements 1 and 3, while the other light source *6b* is common to the other pair of elements 2 and 4.

Figure 1:
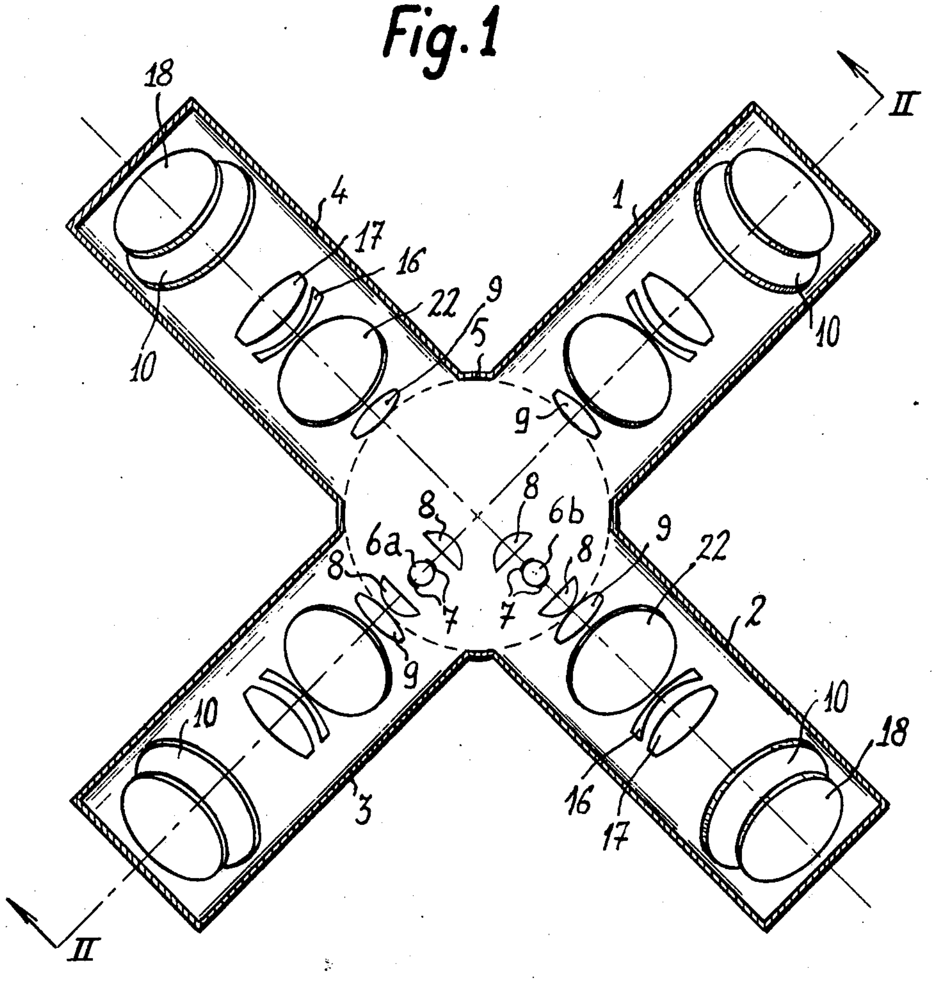
FIG. 1 is a diagrammatic view of the lighting projector shown in section taken along a horizontal plane.

As clearly shown in FIG. 1, the first light source *6a* is disposed on the side of one of the two basic elements of the corresponding pair, namely the adjacent element 3. The other light source *6b* is adjacent another basic element 2.

On either side of each light source a pair of frosted zones 7 located in close vicinity thereof are provided. In actual practice, each frosted zone may be formed on the transparent envelope of the corresponding electric bulb *6a* or *6b*, said zones being obtained by grinding or frosting the glass or quartz bulb constituting said envelope.

Due to this eccentric arrangement of the two light sources *6a* and *6b*, the paths of the light beams formed thereby in a same pair of aligned basic elements have unequal lengths.

Each basic element of the projector according to this invention comprises a condenser-type optical system consisting of a pair of lenses 8 and 9. Due to the specific arrangement contemplated for the light sources, the disposition of the two corresponding lenses differs in the two component elements of a same pair (see FIG. 1) on account of the difference between the paths of the light beams.

At the outer end, each basic element comprises a reflection mirror 10 inclined towards an aperture 11 formed in the wall of the tubular casing of the relevant element. The angle of inclination of said mirrors 10 thus provided at the tip of the various elements 1, 2, 3 and 4 is such that the light beams 12 issuing therefrom converge towards the field or area 13 to be illuminated. The axis 14 of these four light beams are disposed on generatrices of a common cone having its vertex 15 located centrally of the illuminated field 13.

Upstream of the reflection mirror 10 each basic element of this lighting projector comprises an optical system adapted to form the image of the corresponding frosted zone 7 in the plane 13 of the illuminated field, after its reflection by said mirror 10. In the embodiment illustrated, this optical system comprises a pair of lenses 16 and 17.

Figure 2:
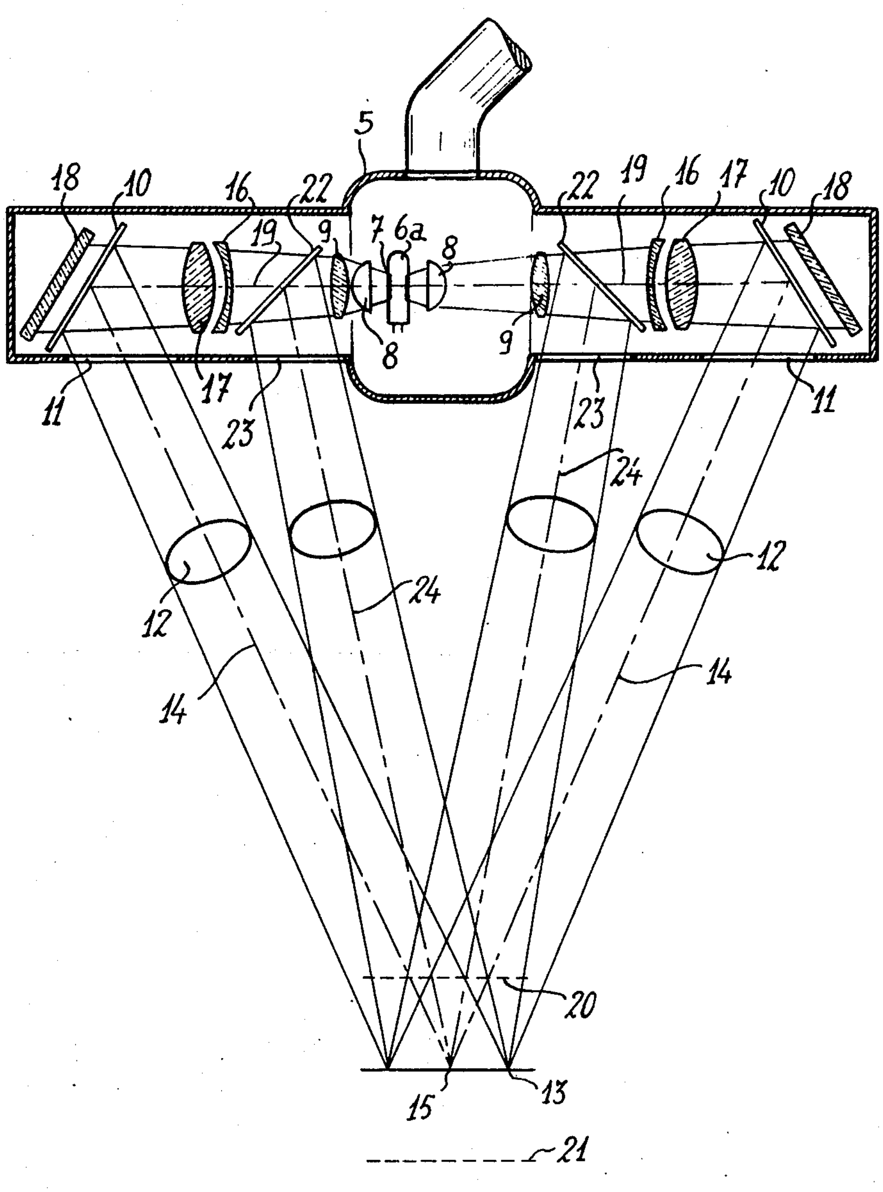
FIG. 2 is a fragmentary vertical section taken along the line II—II of FIG. 1, this view constituting a clear explanatory diagram concerning the mode of operation of one of the basic elements of the lighting projector.
Figure 4:
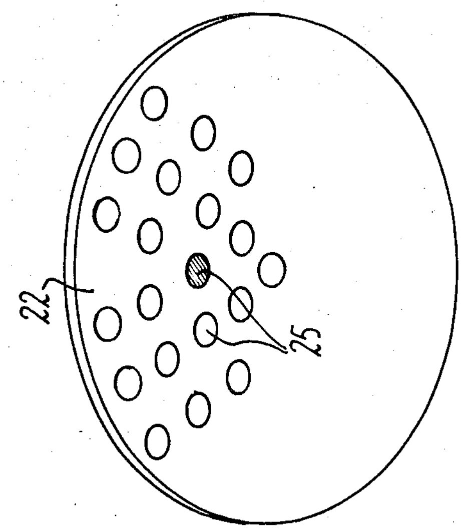
FIG. 4 is a plane view from above of the same additional mirror.
Figure 3:
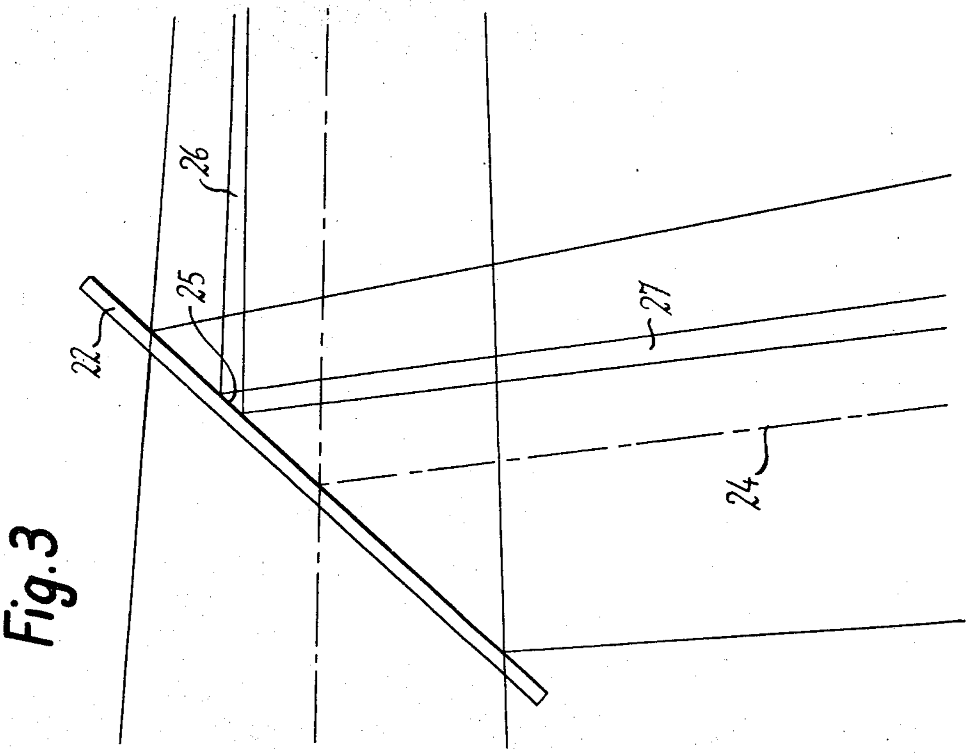
FIG. 3 is a diagrammatical view illustrating the mode of operation of the additional reflection mirror incorporated in said basic element.

The reflecting surface of mirror 10 comprises a complex system of thin interferential layers whereby only the light rays can be reflected while the heat rays are allowed to pass therethrough. Thus, these heat rays pass each through said mirrors 10 and are received by an end element 18 acting as a radiator so as to dissipate said heat rays. Therefore, only the light energy is reflected towards the field 13 to be illuminated. Preferably, the inclinaton of the reflection mirror 10 is adjustable in relation to the axis 19 of the initial light beam, so that the light energy can be focused onto an illuminated plane 13 which varies in position between two endmost parallel planes 20 and 21 (FIG. 2).

According to an original feature characterising the lighting projector according to this invention, each basic element thereof comprises an additional reflection mirror 22 interposed between the optical condensing system 8, 9 and the optical lens system 16, 17. This additional mirror is inclined towards an aperture 23 formed in the lower portion of the tubular casing of the corresponding element. Moreover, its inclination is such that the axis 24 of the light beam reflected by said mirror is focused onto the field 13 to be illuminated (FIG. 2).

However, the mirrors 22 of the various elements 1, 2, 3 and 4 of the instant projector have a specific design in that they reflect only one portion of the light rays while allowing the remaining portion thereof to pass so that this fraction can strike the corresponding endmost reflection mirror 10. For this purpose, each mirror 22 consists of a plate of glass or other suitable transparent material carrying a series of reflecting areas or zones 25 separated from one another by completely transparent areas permitting the free passage of the light rays, and also of the heat rays, in the direction of the corresponding endmost mirror 10. This constitutes so to say a patterned or raster-type reflecting surface.

However, the zones 25 are made in the same fashion as the reflecting surfaces of the endmost mirrors 10. In fact, each zone 25 comprises a complex assembly of thin interferential layers reflecting only the light rays while permitting the passage of the heat rays, so that said heat rays eventually strike the endmost element 18 acting as a heat-dissipating radiator.

Under these conditions, considering now a beam 26 of light and heat rays issuing from the corresponding light source and impinging against one of the reflecting zones 25 of mirror 22, the corresponding light rays are reflected downwards in the form of a light beam 27. On the other hand, the heat rays contained in said beam 26 pass through the mirror 22 and then through the endmost mirror 10 of the corresponding element, until they strike the radiator 18.

Therefore, each additional mirror 22 is adapted to split simultaneously the incoming rays at two different levels, so that:

at a spectral level, the reflecting zones 25 separate the light rays from the heat rays and reflect only the light spectrum while permitting the passage of the heat radiation through said zones, and at a space level, the transparent areas separating the reflecting zones 25 permit the free passage of both light rays and heat rays received by said zones 25.

The amount of light eventually received by the field 13 to be illuminated is substantially the same as if said additional reflection mirror 22 had not been provided, however, the number of light beams striking such field under different angles is doubled. Consequently, this will assis in further reducing to a considerably greater extent the risk of having cast shadows, without inasmuch increasing the number of basic elements of the lighting projector. On the other hand, as already mentioned in the foregoing, an essential advantage characterising this invention is that the lighting projector constituting the subject-matter thereof comprises a reduced number of light sources and nevertheless a sufficient number of basic elements.

Of course, the lighting projector according to this invention should not be construed as being strictly limited by the specific form of embodiment shown and described herein, since various modifications and variations may be brought thereto without departing from the basic principles of the invention as set forth in the appended claims.

What is claimed as new is:

1. Lighting projector comprising a star-shaped arrangement including a plurality of basic elements of elongated configuration, rigid with a casing disposed in the central portion of said projector and extending radially from said central portion, said basic elements being distributed by pairs and in relative alignment in each pair but on either side of said central casing, a common light source being provided for the two elements of a same pair and disposed on the side of one of the two elements involved, a pair of frosted zones being disposed on either side, and in close vicinity, of said common light source, each basic element comprising a reflection mirror located at its outer end opposite said central casing and inclined towards the surface to be illuminated, and also an optical system adapted to form the image of said light source on the field to be illuminated after reflecting said image on said inclined reflection mirror.

* * * * *